United States Patent [19]

Bröcker et al.

[11] Patent Number: 5,750,806
[45] Date of Patent: May 12, 1998

[54] PREPARATION OF ALKENES BY PARTIAL HYDROGENATION OF ALKYNES OVER FIXED-BED PALLADIUM CATALYSTS

[75] Inventors: Franz Josef Bröcker, Ludwigshafen; Manfred Stroezel, Ilvesheim; Udo Rheude, Otterstadt, all of Germany

[73] Assignee: BASF Aktiengesellschaft, Ludwigshafen, Germany

[21] Appl. No.: 679,118

[22] Filed: Jul. 12, 1996

[30] Foreign Application Priority Data

Jul. 20, 1995 [DE] Germany .................. 195 26 473.8

[51] Int. Cl.$^6$ .................................................. C07C 29/17
[52] U.S. Cl. ........................................ 568/909.5; 502/326
[58] Field of Search ........................ 568/909.5; 502/326; 585/250, 528

[56] References Cited

U.S. PATENT DOCUMENTS

| | | |
|---|---|---|
| 2,681,938 | 6/1954 | Lindlar . |
| 4,001,344 | 1/1977 | Hoffman et al. . |
| 4,570,025 | 2/1986 | Nowack et al. . |
| 5,521,139 | 5/1996 | Brocker . |

FOREIGN PATENT DOCUMENTS

| | | |
|---|---|---|
| 0 198 435 | 10/1986 | European Pat. Off. . |
| 0 412 415 | 2/1992 | European Pat. Off. . |
| 24 31 929 | 7/1974 | Germany . |
| 26 19 660 | 11/1976 | Germany . |
| 31 43 647 | 5/1983 | Germany . |
| 871804 | 6/1961 | United Kingdom . |

OTHER PUBLICATIONS

M. Freifelder, "Practical Catalytic Hydrogenation", Wiley-InterScience, New York, 1971 pp. 84–126.
Patent Abstracts of Japan, vol. 007, No. 043, (C-152), Feb. 19, 1983, JP 57 193419, Nov. 27, 1982.
Database WPI, Derwent Publications, AN 84–045214, JP 59 005 127, Jan. 12, 1984.

*Primary Examiner*—C. Warren Ivy
*Assistant Examiner*—Jean F. Vollano
*Attorney, Agent, or Firm*—Oblon, Spivak, McClelland, Maier & Neustadt, P.C.

[57] ABSTRACT

Alkenes are prepared by partial hydrogenation of alkynes in the liquid phase over palladium catalysts by a process which comprises A. using a fixed-bed catalyst which is obtainable by heating the preferably metallic carrier in the air, cooling, coating under reduced pressure with metallic palladium, suitable molding and processing to a monolithic catalyst elements and B. adding from 10 to 180 ppm of CO to the hydrogen used for the hydrogenation.

16 Claims, No Drawings

PREPARATION OF ALKENES BY PARTIAL HYDROGENATION OF ALKYNES OVER FIXED-BED PALLADIUM CATALYSTS

The present invention relates to a technically very advantageous process for the preparation of alkenes, in particular of monosubstituted alkenes, by partial hydrogenation of the corresponding alkynes in the liquid phase over fixed-bed palladium supported catalysts with the addition of carbon monoxide (CO) to the hydrogen used for hydrogenation.

The hydrogenation of alkynes to alkenes is the subject of an extensive prior art.

For example, GB-A 871 804 describes an improved partial hydrogenation of acetylene compounds by a suspension procedure using a Pd catalyst which was treated with salt solutions of the metals Zn, Cd, Hg, Ga, In or Tl.

Furthermore, DE-A 24 31 929 describes a process for the preparation of but-2-ene-1,4-diol by hydrogenation of butynediol in aqueous solution over a catalyst which contains Pd and one of the elements Zn or Cd and at least one of the elements Bi or Te. The catalyst support used is pumice or alumina.

Lead-doped Pd catalysts, ie. Lindlar catalysts, are usually used for the partial hydrogenation of the triple bond in vitamin and scent intermediates, as described, for example, in U.S. Pat. No. 2,681,938. Said catalysts are often deactivated by means of sulfur compounds in order to increase the selectivity (JP-A 120 657/81).

Finally, DE-A 26 19 660 discloses a process for the preparation of butenediol, in which butynediol is hydrogenated in an inert solvent in the presence of a catalyst which contains metallic Pd treated with carbon monoxide. This process can additionally be carried out in the presence of from about 200 to 2000 ppm of CO in the hydrogen used for hydrogenation.

The use of a $Pd/BaSO_4$ catalyst for the preparation of butenediol is also disclosed in DE-A 26 05 241.

M. Freifelder, Practical Catalytic Hydrogenation, Wiley-Interscience, New York, 1971, pages 84 to 126, gives an overview of the industrially used catalyst systems for the partial hydrogenation of triple bonds to olefinic double bonds.

All processes mentioned have the disadvantage that a suspended catalyst having a high Pd content is used. After the hydrogenation, the catalyst must be separated from the reaction product by settling and filtration.

It has been found that, on an industrial scale, complete removal of the catalyst powder is possible only at very great expense. However, traces of catalyst residues in the end product give rise to difficulties in further processing or in the use of the alkenes for other purposes. Thus, there has been no lack of attempts to develop a fixed-bed catalyst having high abrasion resistance for the partial hydrogenation of the triple bond in alkynes in the liquid phase.

EP-B1-04 12 415 discloses a fixed-bed catalyst for the hydrogenation of 3,7-dimethyloct-1-yn-3-ol (hydrodehydrolinalool) to 3,7-dimethyloct-1-en-3-ol (hydrolinalool), which contains palladium as the active component and metals such as Sn, Pb, Zn, Cd, Sb or Bi as an inhibitor. The monolithic palladium fixed-bed catalysts doped with inhibitors and described in this patent make it possible to replace the disadvantageous suspension procedure by the technically essentially more advantageous trickle-bed or liquid phase procedure over the fixed bed catalyst. The very high abrasion resistance of these catalyst monoliths permits a very high gas and liquid space velocity. Unfortunately, when the process described in this patent was carried out continuously over bismuth-doped palladium fixed-bed catalysts for relatively long periods, it was found that the selectivity of the hydrogenation of hydrodehydrolinalool to hydrolinalool slowly decreases, ie. the reaction product contains increasing amounts of the completely hydrogenated 3,7-dimethyloctan-3-ol. An investigation of the catalysts which were required to be replaced showed that the catalyst had lost its bismuth dopant. Experiments to regenerate these catalysts by impregnation with bismuth compounds and reduction of the latter were not promising since the on-stream times of the catalysts regenerated in this manner were only very short.

It is an object of the present invention to provide fixed-bed catalysts for the preparation of alkenes, preferably monosubstituted alkenes, by partial hydrogenation of the corresponding alkynes, which catalysts have the advantages of the monolithic bismuth-doped palladium catalysts according to EP-B1-04 12 415 but retain their selectivity as far as possible without limit, in the continuous partial hydrogenation of alkynes to alkenes.

We have found that this object is achieved and that, surprisingly, these spent catalysts, ie. monolithic palladium fixed-bed catalysts which have lost their bismuth dopant, can be reused with good selectivity if very small amounts of CO are added to the hydrogen used for the hydrogenation. However, alkynes can be hydrogenated to the corresponding alkenes with good selectivities and very long on-stream times, even over palladium fixed-bed catalysts which were prepared similarly to the process according to EP-B1-04 12 415 but in whose preparation doping with inhibitors and possibly also subsequent heating were dispensed with from the outset, if small amounts of CO are added to the hydrogenation gas.

The present invention accordingly relates to a process for the preparation of alkenes by partial hydrogenation of alkynes in the liquid phase over palladium catalysts at from 20° to 250° C. and $H_2$ partial pressures of from 0.3 to 200 bar, which comprises A. using a fixed-bed supported catalyst which is obtainable by heating the carrier in the air, cooling, coating under reduced pressure with metallic palladium, molding and processing to a monolithic catalyst element and B. adding from 10 to 180 ppm, preferably from 50 to 150 ppm, in particular from 60 to 120 ppm, of CO to the hydrogenation gas.

The process is particularly suitable for the partial hydrogenation of monosubstituted alkynes, such as 3,7-dimethyloct-6-en-1-yn-3-ol (dehydrolinalool), 3,7-dimethyloct-1-yn-3-ol (hydrodehydrolinalool) or 3-methyl-1-butyn-3-ol. The partial hydrogenation of monosubstituted alkynes is known to be substantially more problematic than that of disubstituted alkynes, such as butyne-1,4-diol, since they may react further during the hydrogenation. However, the partial hydrogenation of disubstituted alkynes, such as butyne-1,4-diol, is also possible by the novel process.

Examples of starting materials for the novel process are: monosubstituted alkynes, such as dehydrolinalool, hydrodehydrolinalool, 2-methylbutyn-3-yn-2-ol, 3-methyl-1-butyn-3-ol, 1-ethynyl-2,6,6-trimethylcyclohexanol and 17-ethynylandrost5-ene-3β,17β-diol; and disubstituted alkynes, such as butyne-1,4-diol, but-2-yn-1-ol, hex-3-yn-1-ol, 2-hydroxypent-3-yne, 2-hydroxyhex-3-yne, 6-methyl-2-hydroxyhept-3-yne, 4-phenyl-2-hydroxybut-3-yne, 3-methyl-3-hydroxyhex-4-yne, 4-methyl-4-hydroxydec-2-yne, 2,5-dimethylhex-3-yne-2,5-diol, 1,1-diethoxyoct-2-yne, 5-diethylamino-2-hydroxypent-3-yne and bis (tetrahydro-2-pyranyloxy)but-2-yne.

Woven fabrics of inorganic materials, such as $Al_2O_3$ and/or $SiO_2$ or woven fabrics of wires comprising plastics, such as polyamides, polyesters, polypropylene, polytetrafluoroethylene, etc. may be used as the catalyst carrier. However, foil-like or fabric-like metal carriers, ie. foils or woven wire fabrics comprising metals such as iron, spring steel, copper, brass, aluminum, nickel silver, nickel, chromium steel or chromium nickel steels, are particularly suitable. Foils or woven fabrics of materials having the material numbers 1.4767, 1.4401 and 1.4301 have proven particularly useful. The designation of these materials with the stated material numbers is in line with the material numbers stated in the Stahleisenliste, published by the Verein Deutscher Eisenhüttenleute; 8th edition, pages 87, 89 and 106, Verlag Stahleisen mbH, Düsseldorf 1990. The material having material number 1.4767 is also known under the name kanthal. These metallic carriers are pretreated by oxidative heating, preferably in the air at from 600° to 1100° C., preferably from 700° to 1000° C., and then coated with palladium under reduced pressure.

The coating with palladium is carried out by vapor deposition or by sputtering under reduced pressure, ie. at from $10^{-2}$ to $10^{-10}$, preferably from $10^{-3}$ to $10^{-6}$, mbar. Suitable vapor deposition methods under reduced pressure are all known coating processes, in particular thermal evaporation. However, flash evaporation, cathode sputtering and sputtering may also be used. Thermal evaporation can be affected by direct or indirect heating. Electron beam evaporation is preferably used. In this method, the metal to be evaporated is heated superficially in a crucible by means of an electron beam to such an extent that it evaporates. For further details of the methods for vapor deposition and sputtering of metals under reduced pressure, reference may be made to Handbook of Thin Film Technology, Verlag Maissel and Gang, Mc Graw Hill, New York, 1970; Thin Film Processes by J. L. Vossen and W. Kern, Academic Press, N.Y., and EP-A-01 98 435, which is hereby incorporated by reference.

The carrier is advantageously coated by vapor deposition under reduced pressure in thin films, ie. coverings having a thickness of from 0.2 to 100 nm, preferably from 0.5 to 20 nm.

The carrier coated in this manner with palladium can then be formed by heating at from 200° to 800° C., preferably from 300° to 700° C., for from 0.5 to 2 hours. Depending on the type of palladium coating, this heating step after coating may however also be dispensed with. The catalyst foils, catalyst nets or catalyst fabrics coated in this manner with palladium and if necessary subsequently heated are then advantageously shaped in a manner known per se to give monoliths or moldings, for example Sulzer packings, for installation in the hydrogenation reactor. This makes it possible to establish the desired good flow conditions in the reactor.

After the reduction of the catalyst with hydrogen at from 20° to 250° C., preferably from 100° to 200° C., which is advantageously carried out in the reactor, the catalyst is ready for use for the novel partial hydrogenation.

The novel process is advantageous if the partial hydrogenation is carried out continuously in a tube reactor by the trickle-bed or liquid phase procedure with product recycling and with cross-sectional loadings of from 20 to 300, preferably from 100 to 250, $m^3/m^2 \cdot h$.

It is also very advantageous if the hydrogenation gas mixture comprising hydrogen and CO is circulated and the rate of hydrogen absorption, and hence the selectivity, are regulated by means of the CO metering.

The partial hydrogenation is particularly advantageous on an industrial scale if it is carried out by the liquid phase procedure and the hydrogenation gas is sprayed in very fine distribution into the reactor by means of the liquid stream and a suitable apparatus, such as a liquid/gas compressor. In conjunction with the shaping of the catalyst monoliths and the described gassing of the reactor, high space-time yields are achieved by optimum cross-mixing and good hydrodynamics at the catalyst interface. The partial hydrogenations are carried out at from 20° to 250° C., preferably from 60° to 100° C., depending on the substance.

The partial hydrogenation is advantageously carried out continuously in one or more reactors connected in series. The hydrogen partial pressure is from 0.3 to 200, preferably from 0.5 to 20, bar. The hydrogenations can be carried out with or without exit gas. The rate of the $H_2$ absorption can be regulated very easily via the CO metering, which is a considerable technical advance. With the aid of the novel process, it is possible to prepare many alkenes required as scents or intermediates, in particular monosubstituted alkenes, such as linalool, hydrolinalool or 3-methylbut-1-en-1-ol, from the corresponding alkynes in good yields and good space-time yields and with constant good selectivities, also on an industrial scale, in a continuous process over catalysts which can be relatively easily prepared, contain only a small amount of Pd and are stable over long periods.

The procedure for the catalyst preparation and that for the novel partial hydrogenation are illustrated in comparison with those according to the most closely related prior art, by means of the following examples.

EXAMPLE 1

(Comparative Example)

A. Catalyst preparation

A smooth woven stainless steel fabric (material 1.4767) having a mesh size of 180 μm and a wire diameter of 110 μm was cleaned in an ultrasonic bath and then heated in the air for 7 hours (h) at 900° C. A 20 cm wide fabric strip was clamped on the winding apparatus installed in an ultra high vacuum vapor deposition unit and then coated continuously with 2 nm of Pd at $10^{-6}$ mbar by vapor deposition. By rewinding the fabric, the latter was coated with 0.7 nm of Bi in a second vapor deposition step. After the vapor deposition, the catalyst intermediate was formed for 30 minutes (min) at 600° C. in an electric muffle furnace. For this purpose, the heating oven was heated to 600° C. in the course of 40 minutes, kept at this temperature for 30 minutes and then switched off. After cooling, the catalyst was removed from the muffle furnace and shaped into a monolith. This was done by imparting a wavy shape to 41.5 cm of smooth fabric by means of a gear roll, combining said fabric with 38 cm of smooth fabric and winding the fabrics. A monolithic catalyst having a volume of 76 $cm^3$ was obtained in this manner.

B. Selective hydrogenation of 2-dehydrolinalool (2-DHL) to 2-linalool (2 LIN) in the absence of CO.

1 $m^3$ of the Pd/Bi catalyst prepared according to Example 1A, in the form of metal monoliths having a diameter of 600 mm and a height of 200 mm, was introduced into a tube reactor. 2-DHL was passed over the catalyst by the liquid phase procedure, with recycling at a cross-sectional loading of 200 $m^3/m^2 \cdot h$. Hydrogen was circulated at a partial pressure of 2 bar, simultaneously with the liquid stream. At 90° C., a space-time yield of 0.37 $l/l_{car} \cdot h$ was obtained at 100% conversion and overhydrogenation of only 1.35%.

However, it was found that the overhydrogenation increased in the course of time. It reached a value of 4.98% after 46 days and of 6.37 % after 131 days. Investigation of the catalyst showed that, under these reaction conditions, the Bi used as inhibitor had been completely discharged from the catalyst and the latter had thus lost its selectivity.

EXAMPLE 2

A. Catalyst preparation

The same smooth stainless steel fabric as in Example 1A was cleaned in an ultrasonic bath and then heated in the air for 7 hours at 900° C. A 20 cm wide fabric strip was clamped on the winding apparatus installed in a UHV vapor deposition unit and then coated continuously with Pd at $10^{-6}$ mbar by vapor deposition. The catalyst was then shaped into a monolith as described in Example 1A.

B. Selective hydrogenation of 2-DHL to 2-LIN over a Pd catalyst in the presence of CO 1 $m^3$ of the Pd catalyst prepared according to Example 2A, in the form of metal monoliths having a diameter of 600 mm and a height of 200 mm, was introduced into the same tube reactor as in Example 1B. 2-DHL was passed over the catalyst similarly to Example 1B by the liquid phase procedure with recycling with a cross-sectional loading of 200 $m^3/m^2$.h. Hydrogen to which 70 ppm of CO had been added was circulated at a partial pressure of 1.5 bar, simultaneously with the liquid stream.

The amount of CO in the cycle gas was kept constant. At 90° C., an $H_2$ partial pressure of 1.5 bar and 70 ppm of CO in the cycle gas, overhydrogenation of 1.2% was obtained at a space-time yield of 0.31 $l/l_{cat}.h$ and at a conversion of 100%. After an on-stream of 100 days, the overhydrogenation at 100% conversion was constant at 1.2%. No further aging of the catalyst was observed.

We claim:

1. A process for the preparation of an alkene comprising:
   hydrogenating an alkyne in the liquid phase over a palladium catalyst at 20°–250° C. and a hydrogen partial pressures of 0.3 to 200 bar,
   wherein said catalyst is a fixed bed supported catalyst which is obtained by heating a carrier in air, cooling, coating under reduced pressure with metallic palladium, molding and processing to monolithic catalyst elements; and
   wherein 10–80 ppm of carbon monoxide is added to hydrogen used for said hydrogenation.

2. A process as claimed in claim 1, wherein a supported catalyst comprising a metallic carrier in the form of a woven metal fabric or a metal foil is used.

3. A process as claimed in claim 1 which is used for the preparation of a monosubstituted alkene from the corresponding 1-alkyne.

4. A process as claimed in claim 3, which is used for the preparation of 3,7-dimethyloct-1,6-dien-3-ol, 3,7-dimethyloct-1-en-3-ol or 3-methylbut-1-en-3-ol from the corresponding alkynes.

5. A process as claimed in claim 1, wherein the hydrogenation is carried out in a tube reactor by the trickle-bed or liquid phase procedure with product recycling and with cross-sectional loadings of from 20 to 300 $m^3/m^2$.h.

6. A process as claimed in claim 5, wherein a hydrogenation gas mixture comprising hydrogen and carbon monoxide is circulated and hydrogen absorption, and hence the selectivity, are regulated by means of the carbon monoxide metering.

7. A process as claimed in claim 5, wherein the hydrogenation is carried out by the liquid phase procedure and hydrogenation gas is sprayed in very fine distribution into the reactor by means of a suitable apparatus.

8. A process as claimed in claim 1, wherein the hydrogenation is carried out at from 60° to 150° C.

9. A process as claimed in claim 1, wherein the hydrogenation is carried out at a hydrogen partial pressure of from 0.5 to 20 bar.

10. A process as claimed in claim 1, wherein the hydrogenation is carried out continuously in one or more reactors connected in series.

11. A process as claimed in claim 1, wherein a fixed-bed supported catalyst is used which is obtained by heating a carrier which is coated with palladium by vapor deposition.

12. The method of claim 1, wherein said catalyst is prepared without doping with an inhibitor.

13. The process of claim 1, wherein said catalyst is obtained by heating a carrier in air, cooling, coating under reduced pressure with a material which consists essentially of metallic palladium, molding and processing to monolithic catalyst elements.

14. The process of claim 1, wherein said catalyst is obtained by heating a carrier in air, cooling, coating under reduced pressure with a material which consists of metallic palladium, molding and processing to monolithic catalyst elements.

15. The process of claim 1, wherein said process is carried out continuously.

16. A process for the preparation of an alkene comprising:
   hydrogenating an alkyne in the liquid phase over a palladium catalyst at 20°–250° C. and a hydrogen partial pressures of 0.3 to 200 bar, in a tube reactor by the trickle-bed or liquid phase procedure with product recycling and with cross-sectional loadings of from 20 to 300 $m^3/m^2$.h,
   wherein said catalyst is a fixed bed supported catalyst which is obtained by heating a carrier in air, cooling, coating under reduced pressure with metallic palladium, molding and processing to monolithic catalyst elements; and
   wherein 10–180 ppm of carbon monoxide is added to hydrogen used for said hydrogenation,
   wherein a hydrogenation gas mixture comprising hydrogen and carbon monoxide is circulated and hydrogen absorption, and hence the selectivity is regulated by means of carbon monoxide metering.

* * * * *